United States Patent [19]

Lundmark et al.

[11] 4,065,422

[45] Dec. 27, 1977

[54] HIGH SLIP POLYMER COMPOSITION CONTAINING A POLYACRYLAMIDO SULFONIC ACID SALT AND AN ALCOHOL

[75] Inventors: Larry D. Lundmark, Richfield; Allan Melby, Andover; Ho-ming Chun, New Brighton, all of Minn.

[73] Assignee: General Mills Chemicals, Inc., Minneapolis, Minn.

[21] Appl. No.: 769,353

[22] Filed: Feb. 16, 1977

[51] Int. Cl.$^2$ .............................................. C08L 33/02
[52] U.S. Cl. ............................ 260/29.6 E; 252/48.6; 252/49.3; 252/49.5; 260/29.5 SQ; 260/29.6 HN; 260/29.6 ME; 260/33.4 R; 260/79.3 MU; 424/78; 424/81
[58] Field of Search ................................. 424/78, 81; 260/29.6 SQ, 29.6 E, 29.6 ME, 79.3 MU, 33.4 R, 29.6 HN; 252/48.6, 49.3, 49.5

[56] References Cited

U.S. PATENT DOCUMENTS

| | | | |
|---|---|---|---|
| 3,238,141 | 3/1966 | Gatza | 260/29.6 SQ |
| 3,275,561 | 9/1966 | Pye et al. | 252/110 |
| 3,332,904 | 7/1967 | La Combe et al. | 260/79.3 MU |
| 3,897,348 | 7/1975 | Atkinson | 252/8.75 |
| 3,899,566 | 8/1975 | Murray | 264/245 |
| 3,931,089 | 1/1976 | Karl | 260/29.6 SQ |
| 3,963,649 | 6/1976 | Spadini et al. | 252/546 |
| 3,984,536 | 10/1976 | Viout et al. | 260/33.4 R |

FOREIGN PATENT DOCUMENTS

| | | |
|---|---|---|
| 864,433 | 2/1971 | Canada. |
| 2,153,292 | 5/1972 | Germany. |
| 404,109 | 5/1943 | Italy. |

*Primary Examiner*—Eugene C. Rzucidlo
*Attorney, Agent, or Firm*—Gene O. Enockson; Patrick J. Span; Forrest L. Collins

[57] ABSTRACT

This invention relates to compositions which may be used on keratinous substrates such as skin or hair or upon mucous membranes to impart a highly lubricated feel thereon. Such compositions have utility in diverse personal care products as hand and body creams, soap bars, suntan lotion, preelectric shave skin conditioners, after shave lotions, lip balms, cold creams, bubble baths, cleansing and lotion pads, and household cleaning products as well as many other similar compositions.

7 Claims, No Drawings

HIGH SLIP POLYMER COMPOSITION CONTAINING A POLYACRYLAMIDO SULFONIC ACID SALT AND AN ALCOHOL

BACKGROUND OF THE INVENTION

1. Field of the Invention

The present invention relates to alcohol based personal care products which impart a feeling of lubricity to the contacted substrate.

2. Description of the Art

Alcohol based personal care products are widely marketed. Such alcoholic formulations are ordinarily prepared such that the alcohol is a carrier or solvent for the remainder of the composition or in the case of higher molecular weight alcohols such as cetyl or stearyl alcohol to provide not only a carrier but also to give an emollient effect upon the skin. In addition to emolliency it is desireable that alcoholic personal care formulations be able to impart a feeling of lubricity or silkiness to the skin or hair. Aside from the general "good" feeling such compositions also provide sheen and manageability to the hair.

It is now been found useful to incorporate into alcoholic personal care formulations high molecular weight polymeric salts of 2-acrylamido-2-methylpropane sulfonic acid to provide a lubricated feel.

Previous uses of 2-acrylamido-2-methylpropane sulfonic acid polymers have been for non-personal care products. For instance, German OLS No. 2,153,292 laid open for inspection May 4, 1972 suggests the use of similar polymers to thicken water-based hydraulic fluids containing glycols or ether derivatives. Such polymers have also been known as described in U.S. Pat. No. 3,931,089 issued Jan. 6, 1976 to Karl as thickeners for acid solutions having a pH value of about 2 or below.

Related but structurally dissimilar polymers have stated uses as emulsifiers, thickeners, adhesives, dye equalizers, and color printing agents as described in Italian Patent 404,109 issued May 21, 1943.

Interpolymers of acrylamido-aklylsulfonates are described in U.S. Pat. No. 3,332,904 issued July 25, 1967 to La Combe et al for use as detergents and flexible films. In the U.S. Pat. No. 3,275,561 to Pye et al issued Sept. 27, 1966 compositions are described containing acrylamides to improve the lubricity of shaving soaps. Thickened salt solutions containing alcohols and vinyl aromatic sulfonate polymers are described in U.S. Pat. No. 3,238,141 issued to Gatza on Mar. 1, 1966.

While certain homopolymers and copolymers of 2-acrylamido-2-methylpropane sulfonic acid are known it has not been previously suggested to incorporate such materials into alcoholic personal care products to provide a high degree of lubricity.

SUMMARY OF THE INVENTION

A composition of matter which imparts lubricity is prepared comprising:
  a. from about 0.01% to about 50% by weight of a salt of

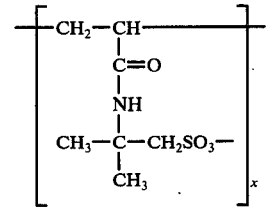

wherein x has a value such that the molecular weight of the anionic portion of the polymer is from about 1,000,000 to about 5,000,000 and;
  b. from about 99.99% to about 1.0% by weight of a monohydric alcohol. The above composition may be varied to provide a high viscosity aqueous formulation by including as component
  c. from about 1% to about 90% by weight water.

Throughout the specification and claims, percentages and ratios are by weight and temperatures are in degrees Celsius unless otherwise indicated.

DETAILED DESCRIPTION OF THE INVENTION

The materials which have been found to lubricate keratinousness substrates such as skin or hair are polymers of 2-acrylamido-2-methylpropane sulfonate. The preparation of such polymers is described in Canadian Patent 864,433 issued Feb. 23, 1971 and in German OLS No. 2,153,292 laid open May 4, 1972 both of which are herein incorporated by reference.

The lubricating polymer of the present invention has the repeating linkage shown in the summary of the invention and is prepared from

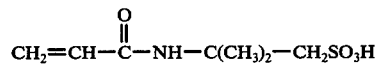

or a salt thereof. The polymerization reaction may be accomplished by solution, emulsion or suspension polymerization processes. The medium for the polymerization is conveniently water, the monohydric alcohol, or a mixture thereof. The choice of the medium is best dictated by the requirements of the final personal care product to be formulated.

The polymerization reaction is described as temperature, pH, and catalyst sensitive. In addition it is desirable to exclude oxygen from the reaction vessel used to form the polymer as that material inhibits the polymerization process. The catalysts which are included to enhance the rate of polymerization are materials such as ammonium bisulfite, ferrous sulfate, hydrogen peroxide, sodium metabisulfite, or other redox catalysts.

The polymer may be varied in molecular weight by controlling the amount of the catalyst, the pH, or the rate of addition of the monomer to the reaction vessel. The polymerization may be facilitated by converting the monomer from its acid form to a salt which is water-soluble. This step is quite desirable in any event as the application of the personal care product of the skin requires that the pH of the personal care product be non-irritating. That is, the in use pH of the personal care product should be from about 3 to about 10, preferably about 4.5 to about 9.0 and most preferably from about 5 to about 8. Thus within the foregoing ranges some of the polymer may be in the acid form. The salts of the polymer preferably contain as cations, sodium, potassium, ammonium, monoethanolamine, diethanolamine, triethanolamine and 2-amino-2-methyl-1-propanol as well as mixtures thereof. The foregoing list is merely exemplary of water-soluble salts which may be used. Also within the scope of the present invention are water-insoluble salts where the personal care product is not adversely affected by percipitation of the polymer. Such products where water-insoluble salts of the polymer may be utilized are soap bars, or substantially non-aqueous products such as body lotions. Examples of suitable water-insoluble salts are calcium and magnesium.

As was previously mentioned the molecular weight of the polymer may be controlled by the pH, the rate of addition of the monomer or the judicious use of the catalyst. It has been found desirable to utilize the afore-described polymers having a molecular weight of from about 1,000,000 to about 5,000,000 more preferably from about 2,500,000 to about 4,500,000 to increase the asthetics of the personal care compositions. That is, it has been found that extremely high molecular weight polymers of the type described may result in a pituitive or stringy consistency of the end product. It has therefore been found desirable to limit the pituitivness by selecting the preferred molecular weight range. To this end any common chain transfer agent such as mercaptosuccinic acid may be used to limit the molecular weight of the polymer.

It is noted that the terminal groups on the polymer have little bearing on the desired properties of the personal care products and are thus not specified. In the interest of complete disclosure it is noted that the terminal groups are most often hydrogen, but may also be hydroxyl, sulfate, sulfonate or

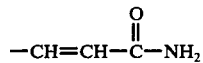

The monohydric alcohol component of the present invention is preferably limited to those alcohols ($C_1$-$C_{24}$) which are non-irritating to the skin or hair such as methanol, ethanol, isopropanol, propyl, lauryl, myristyl, cetyl, and stearyl as well as mixtures thereof. The choice of the alcohol to be utilized with the particular polymer of the present invention will ordinarily be dictated by product asthetics and physical form of the composition. For instance, where liquid compositions are desired the lower alcohols are preferably utilized while solid or cream compositions within the scope of the present invention will normally require the higher alcohols. Where the personal care formulations of the present invention contain ingredients other than the polymer or the alcohol in substantial amounts the choice of the particular alcohol becomes less important. For example, if the personal care product is to be an abrasive hand cleaning product then a large proportion of the product will be surface active agents and an abrasive such as pumice or sand thereby giving wide latitude to the choice of the particular alcohol.

When it is desired the personal care products of the present invention may be substantially non-aqueous. An important variable which has been discovered is that the polymers contrary to expectation are highly soluble in monohydric alcohols. That is, it was highly unexpected that the polymers of the present invention would be soluble to any degree in alcohol considering the molecular weight of the polymer and the fact that acrylamide polymers of similar weight are considerably less soluble in alcohols. It is not necessary, however, that the polymer be soluble in the alcohol as long as it is dispersible.

Therefore in the present invention the polymer is ordinarily present at from about 0.01% to about 50% by weight, preferably from about 0.1% by weight to about 10% by weight most preferably from about 0.5% by weight to about 5% by weight. The amount of the monohydric alcohol used is from about 1% to about 99.99% preferably from about 2% to about 40%, most preferably from about 3% to about 30% by weight.

A desirable variable of the present invention is the incorporation of water to a mixture of the polymer and the monohydric alcohol with a resultant increase in viscosity over that which would be expected based on the viscosity of the polymer and the monohydric alcohol alone thus giving wide latitude in formaulating the personal care products. The particular weight ratios at which the desirable increase in viscosity occurs for mixtures of the polymer, monohydric alcohol and water are respectively from about 1:5:80 to about 1:80:5. Preferably this ratio is in the range of from about 1:10:40 to about 1:40:10. Within the aforementioned range highly viscous personal care compositions are obtained with low solids content. Such compositions are desirable in that they allow compositions such as suntan or body lotions to be formulated in a thickened state providing greater ease of application.

The personal care products of the present invention as previously indicated may be formulated into such diverse products as soap bars, dishwashing compositions, douches, hand and body lotions, suntan lotion, cold creams, preshave and after shave products as well as cleansing or lotion pads and wound dressings and many other personal care products. Listed below are materials which may be included in such personal care products.

Hand and body lotions frequently contain emollients such as stearic acid, glycerol monostearate, mineral oil, glycerine, sesame oil, beeswax, lauryl, myristyl, cetyl or stearyl alcohols, lanolin, lecithin, sterols, isopropylmyristate, and as well any other art recognized emollients. Emollients are typically used in the present invention at levels of from about 1% to about 50% by weight.

Astringents and antiseptics may be incorporated into the compositions of the present invention. A preferred astringent material is zinc phenolsulfonate. The foregoing material exhibits not only astringent but also antiseptic qualities and is of particular use in preshave formulations to make the beard "stand up". Humicants such as propylene glycol are also desirable ingredients for inclusion in personal care products to prevent drying of the skin. Allantoin is included in such compositions for its perported soothing and healing affects upon injured skin.

The soap bar, dishwashing products and shampoos of the present invention may contain all manner of anionic non-ionic, zwitterionic, ampholytic or cationic surfactants. Typically the surfactant will be present at from about 1% to about 70%, preferably about 3% to about 35% by weight.

Most preferably the dishwashing compositions of the present invention contain anionic surfactants which for example include alkylether sulfates, olefin sulfonates, alkyl and alkenyl sulfates, alkyl sulfonates, and alkylbenzene sulfonates. A particularily useful discovery is that the polymer when used with a surface active agent enhances and prolongs suds life. That is, consumers using dishwashing products often tend to overuse the composition when the suds disappear from the surface of the dishpan. Thus in the surfactant formulations of the present invention the presence of the polymer maintains the suds level thus avoiding inadvertent overuse of the product by the consumer.

The soap bars of the present invention may either contain real soap, combinations of soap and synthetic surfactants or may be formulated solely with synthetic surfactants such as alkylbenzene sulfonates. A more particular disclosure of components which are ordinarily found either as surfactants or additives in dishwashing compositions are more fully described in U.S. Pat. No. 3,963,649 issued June 15, 1976 to Spadini et al herein incorporated by reference. The general method of producing soap or detergent bars which may be formulated in accordance with the present invention is described in U.S. Pat. No. 3,899,566 issued Aug. 12, 1975 to Murray herein incorporated by reference. Shampoo formulations which may be prepared according to the present invention are described in U.S. Pat. No. 3,897,348 herein incorporated by reference issued July 29, 1975 to Atkinson. The following are examples of the present invention.

EXAMPLE I

A polymer of the structural formula

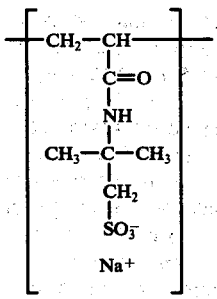

having a molecular weight of about 4,500,000 is prepared in the following manner:

A solution of 90.1 parts (0.437 mole) of 2-acryamido-2-methylpropanesulfonic acid in 100 parts of water is blanketed with nitrogen. 231 parts (0.437 mole) $Na_2CO_3$ is added with stirring. After about 5 minutes of stirring at room temperature the solution becomes very viscous and an exothermic reaction is observed. After 10 minutes the reaction is complete and the product is a clear gel.

EXAMPLE II

A polymer is prepared having the formula described in Example I in the following manner:

45.2 grams of the monomer are neutralized with NaOH in 50 ml $H_2O$. The resultant salt is placed in a resin flask and 0.5 gram sodium lauryl sulfate is added. The mixture is stirred and purged with nitrogen. 0.001 gram each of ammonium persulfate and sodium metabisulfite are added with stirring. 500 grams of benzene are added and the flask is heated to 50° C. Following polymerization, the polymer is washed with dimethyl ketone and dried at 65° C.

The molecular weight of the polymer is determined by its inherent viscosity to be 3,100,000. In similar fashion polymers are prepared having molecular weights of 3,300,000; 3,500,000; and 4,000,000.

EXAMPLE III

A portion of the polymer prepared in Example II having a molecular weight of 3,100,000 is incorporated into a soap bar containing:
 90 parts sodium stearate
 9 parts cetyl alcohol
 1 part polymer
When used as a hand soap the composition provides the skin with a silky feel. Similar results are obtained when the sodium stearate is replaced by sodium dodecyl benzene sulfonate.

EXAMPLE IV

A hand and body lotion is prepared containing:
 1.5% stearic acid
 1.5 glycerol monostearate
 5 mineral oil
 10 lauryl alcohol
 5 sesame oil
 3 Generol 122 (Soya sterol)
 1 triethanolamine
 1 polymer balance water, preservatives, perfumes and minors
The above product when applied to the skin provides a lubricated feel and emollient properties.

EXAMPLE V

Suntan lotions are prepared using each of the polymers in turn of Example I and Example II in the following formulation:
 20% mineral oil
 7% cetyl alcohol
 1.5% Amyl-para-dimethylaminobenzoate (sunscreen)
 3.3% Generol 122 E16 (a soya sterol condensed with 16 moles of ethylene oxide per mole of sterol)
 0.2% allantoin
 2.0% ethanol
 0.5% polymer balance water, perfume and minors
The above compositions are effective suntan lotions which provide a high degree of lubricity when applied to the skin.

EXAMPLE VI

A cold cream base is prepared containing:
 50% mineral oil
 15% Beeswax
 4% Generol 122
 20% polymer (of Example II having a molecular weight of about 4,000,000 neutralized with 2-amino-2-methyl-1-propanol)
 10% cetyl alcohol
 1% sodium borate
This composition imparts a silky feel to the skin when used as a cold cream.

EXAMPLE VII

A cleansing douche is prepared using the polymer of Example I in the following product:
 0.5% polymer (neutralized to pH 6 with triethanolamine)
 5.0% cetyl alcohol
 2.0% sodium dodecylhexethoxysulfate balance water, perfume, colorant
The product cleans effectively while providing lubrication to the mucous membranes.

EXAMPLE VIII

A preshave lotion is prepared containing a polymer as described in Example II having a molecular weight of about 3,500,000 comprising:
15% isopropyl myristate
0.3% polymer balance ethanol The preshave product provides a high degree of lubricity to the skin during shaving with an electric razor thereby lessening razor drag. Substantially similar results are obtained when the ethanol is replaced by isopropanol or the isopropyl myristate is varied between 10–25% and the polymer is at from 0.1 to 1.6%.

EXAMPLE IX

An astringent preshave lotion product is prepared with polymer described in Example VIII comprising:
2% dodecyltetraethoxylated alcohol
0.05% menthol
1.0% zinc phenolsulfonate
1.0% polymer
49.0% ethanol balance water, perfumes and miscellaneous.

The polymer was introduced into the preshave product as a premix by dispersing it in the ethanol. The product is thus stable and the zinc salt does not cause the polymer to precipitate out of the product. The product is a milky lotion having a viscosity of about 1000 cps on a Brookfield viscometer spindle number 2. When compared to a similar product not containing the polymer it is found that the zinc salt does not crystallize on the skin upon evaporation of the solvent thus the skin becomes evenly taut and the beard is easily removed by an electric or safety razor. Again skin drag is reduced by the polymer.

EXAMPLE X

An after shave personal care product is prepared using a polymer having an approximate molecular weight of 3,100,000 prepared in accordance with Example II. The formulation is as follows:
2% Fragrance, Albert Verley No. CS-19611
10% Premix of ethanol containing 1 part acid polymer per 50 parts alcohol
3% propylene glycol
70% ethanol
5% isopropyl myristate
q.s. triethanolamine to pH 4–5 balance water The after shave containing the polymer and humictant (propylene glycol) provides the skin with a silky non-dry feeling following shaving.

EXAMPLE XI

A personal care pad is prepared by applying a mixture containing 2 parts of the polymer of Example I and 98 parts ethanol to cheesecloth substrate. If desired some of the alcohol may be evaporated off the substrate.

A small amount of surfactant such as triethanolamine lauryl sulfate may be added to the pad if cleansing action is desired. Medication may also be added to the pad for use as a bandage which is easily removable.

EXAMPLE XII

A detergent composition useful for washing dishes and tableware is prepared containing the polymer of Example II having a molecular weight of about 3,500,000 comprising:
0.5% polymer
3% ethanol
20% sodium hexaethoxylaurylsulfate balance water The composition cleans the dishware and tableware effectively while imparting a silky feel to the skin. The composition sudses well initially and maintains suds throughout the wash.

What is claimed is:

1. A composition of matter which imparts lubricity comprising:
    a. from about 0.01% to about 50% by weight of a homopolymeric salt of

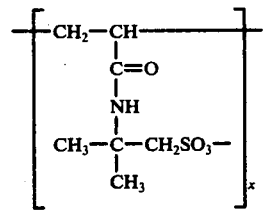

wherein x has a value such that the molecular weight of the anionic portion of the polymer is from about 1,000,000 to about 5,000,000, and;
    b. from about 1% to about 99.99% by weight of a monohydric alcohol wherein the pH of the composition is from about 3 to about 10.

2. The composition of claim 1 wherein the monohydric alcohol is selected from the group consisting of methyl, ethyl, isopropyl, propyl, lauryl, myristyl, cetyl, and stearyl alcohol and mixtures thereof.

3. The composition of claim 1 wherein the molecular weight of the polymer is from about 2,500,000 to about 4,500,000.

4. The composition of claim 1 additionally comprising water in a weight ratio of (a):(b):water of from about 1:5:80 to about 1:80:5.

5. The composition of claim 1 additionally containing a member selected from the group consisting of anionic, nonionic, zwitterionic, ampholytic, and cationic surfactants at from about 1% to about 70% by weight.

6. The composition of claim 1 additionally containing an emollient at from about 1% to about 50% by weight.

7. The composition of claim 1 wherein the cation of the polymer is selected from the group consisting of sodium, potassium, ammonium, monoethanolamine, diethanolamine, triethanolamine, and 2-amino-2-methyl-1-propanol and mixtures thereof.

* * * * *